(12) United States Patent
Butler et al.

(10) Patent No.: US 11,344,436 B2
(45) Date of Patent: May 31, 2022

(54) APPARATUS FOR HIP SURGERY

(71) Applicant: DEPUY IRELAND UNLIMITED COMPANY, County Cork (IE)

(72) Inventors: Lewis Butler, Leeds (GB); Stephanie Prince, Wakefield (GB); Duncan Young, Melbourn (GB)

(73) Assignee: DEPUY IRELAND UNLIMITED COMPANY

( * ) Notice: Subject to any disclaimer, the term of this patent is extended or adjusted under 35 U.S.C. 154(b) by 238 days.

(21) Appl. No.: 16/500,852

(22) PCT Filed: Apr. 9, 2018

(86) PCT No.: PCT/EP2018/059062
§ 371 (c)(1),
(2) Date: Oct. 4, 2019

(87) PCT Pub. No.: WO2018/189125
PCT Pub. Date: Oct. 18, 2018

(65) Prior Publication Data
US 2020/0100917 A1 Apr. 2, 2020

(30) Foreign Application Priority Data

Apr. 12, 2017 (GB) .................................. 1705920

(51) Int. Cl.
*A61F 2/46* (2006.01)
*A61F 2/36* (2006.01)
*A61F 2/30* (2006.01)

(52) U.S. Cl.
CPC .......... *A61F 2/4684* (2013.01); *A61F 2/4607* (2013.01); *A61F 2002/30507* (2013.01);
(Continued)

(58) Field of Classification Search
CPC ..... A61F 2/4684; A61F 2/4607; A61F 2/3609
See application file for complete search history.

(56) References Cited

U.S. PATENT DOCUMENTS 5,163,961 A * 11/1992 Harwin ............... A61F 2/30739
623/22.46
9,308,102 B2 * 4/2016 McCarthy ............. A61F 2/4657
(Continued)

FOREIGN PATENT DOCUMENTS

EP 807426 A2 11/1997
EP 1634551 A2 3/2006
(Continued)

OTHER PUBLICATIONS

Lucas, David H., and Scott, Richard D., *The Ranawat Sign A Specific Maneuver to Assess Component Positioning in Total Hip Arthroplasty*, Journal of Orthopaedic Techniques, vol. 2, No. 2, Jun. 1994.

*Primary Examiner* — Christian A Sevilla

(57) ABSTRACT

Apparatus and Method for Hip Surgery. An adjustable trial femoral head (400) for assessing anteversion of an acetabular cup relative to a pelvis of a patient are described. The adjustable trial femoral head comprises a spherical body (402) having a bore extending along a polar axis of the spherical body and configured to receive a free end of a femoral neck. A visual alignment guide (420) is mounted on the at least partially spherical body and the orientation of the visual alignment guide relative to the spherical body is adjustable.

7 Claims, 10 Drawing Sheets

(52) U.S. Cl.
CPC ........... *A61F 2002/30538* (2013.01); *A61F 2002/30617* (2013.01); *A61F 2002/30822* (2013.01); *A61F 2002/365* (2013.01); *A61F 2002/3611* (2013.01)

(56) References Cited

U.S. PATENT DOCUMENTS

| | | |
|---|---|---|
| 2005/0107799 A1 | 6/2005 | Brack |
| 2007/0162140 A1* | 7/2007 | McDevitt ............ A61F 2/4014 623/18.11 |
| 2008/0021299 A1* | 1/2008 | Meulink ............ A61F 2/0095 600/407 |
| 2011/0093087 A1 | 4/2011 | Allen |
| 2011/0218642 A1 | 9/2011 | Widmer |
| 2014/0249535 A1 | 9/2014 | La Rosa |
| 2016/0220318 A1 | 8/2016 | Falardeau |

FOREIGN PATENT DOCUMENTS

| | | | |
|---|---|---|---|
| WO | WO 2009108683 A1 | 9/2009 | |
| WO | WO 2012125795 A2 | 9/2012 | |
| WO | WO-2013117909 A1 * | 8/2013 | ........... A61F 2/4684 |
| WO | WO 2013117909 A1 | 8/2013 | |
| WO | WO 2014176548 A1 | 10/2014 | |
| WO | WO 2015083116 A1 | 6/2015 | |
| WO | WO 2016014616 A1 | 1/2016 | |

\* cited by examiner

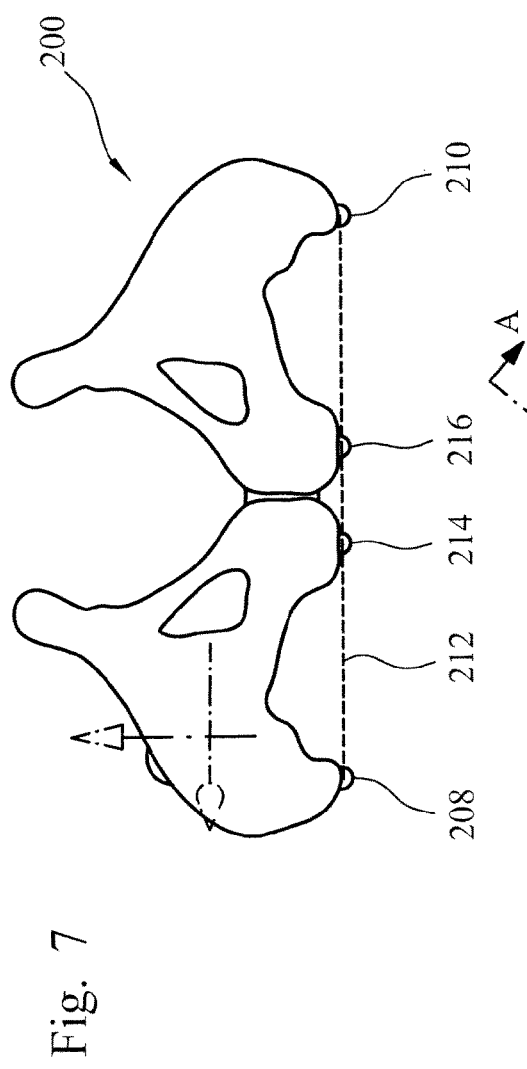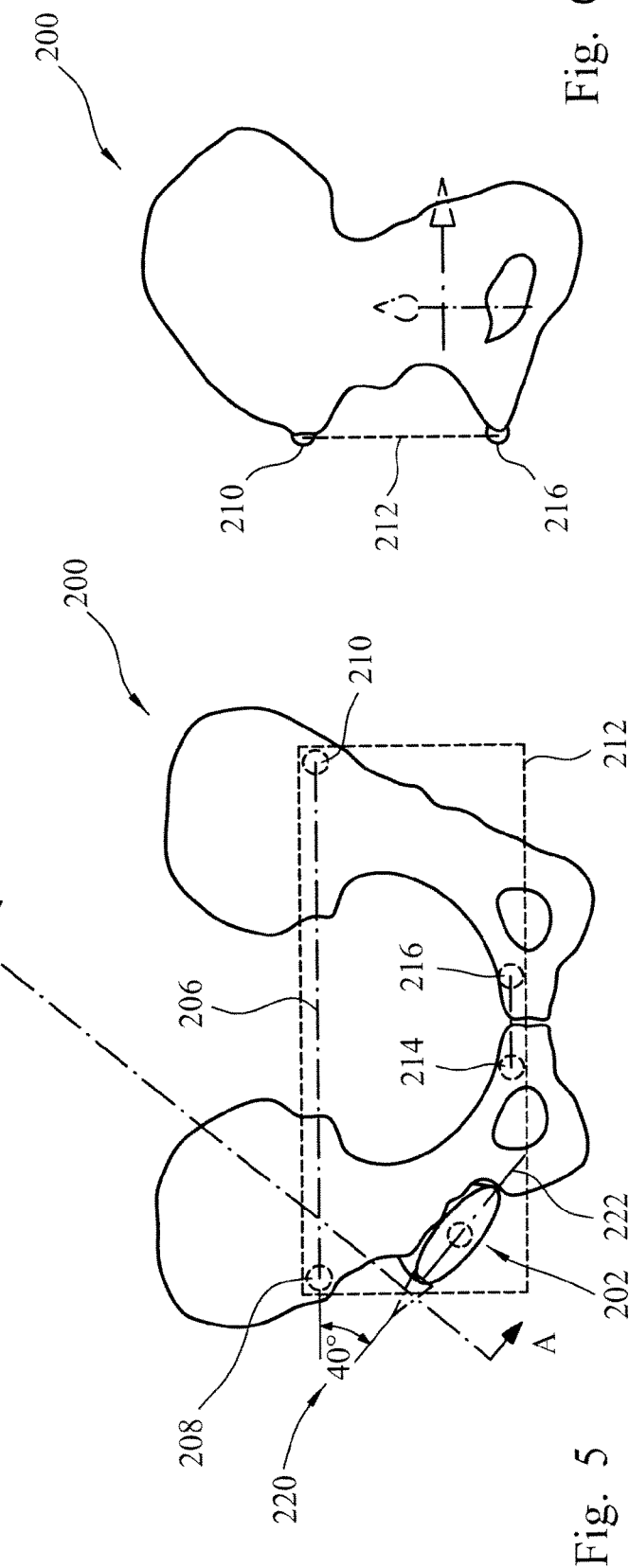
Fig. 7
Fig. 5
Fig. 6

Fig. 8
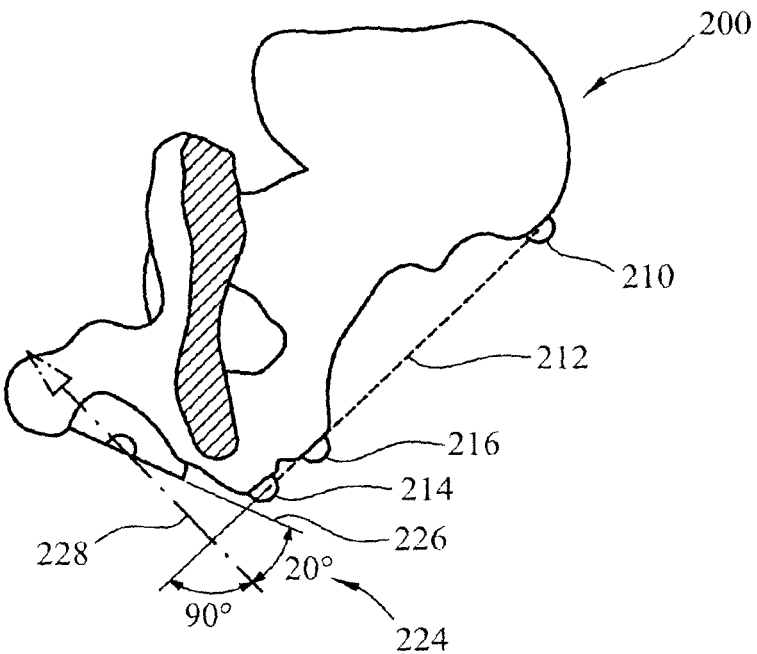
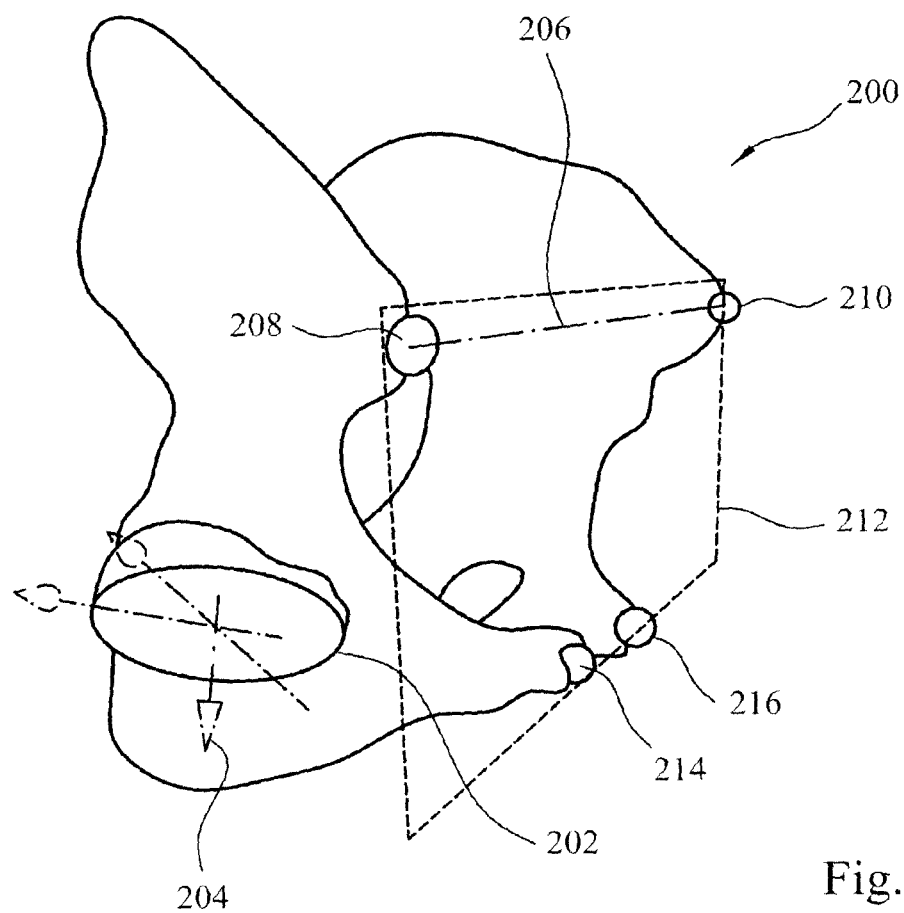
Fig. 9

APPARATUS FOR HIP SURGERY

CROSS REFERENCE TO RELATED PCT APPLICATION

This application is a National Stage 35 U.S.C. 371 of International Patent Application PCT/EP2018/059062 filed Apr. 9, 2018, which claims priority to United Kingdom Application No. 1705920.5, filed Apr. 12, 2017, all of which are incorporated by reference in their entireties.

The present invention relates to apparatus and methods for hip surgery, and in particular to one or more components of a hip joint and/or methods of hip surgery using such components.

A variety of methods of hip surgery are generally known. The hip joint may generally be considered a ball and socket joint in which the head of the femur articulates within the acetabular cavity of the pelvis. Some methods of hip surgery may involve the replacement of one or more parts of the hip joint with one or more prosthetic components. This may be to replace damaged, worn, diseased or otherwise imperfect parts of the hip joint including the respective articulating surfaces of the acetabular cavity and/or femoral head.

Different surgical procedures may involve replacement of a part of the acetabulum or the femoral head or both. Some procedures, sometimes referred to as resurfacing procedures, may involve replacement of only the articulating surface of the femoral head. Other procedures may involve replacement of the entire femoral head. Such procedures often also use a stem component which is implanted in the resected femur and having a neck to which the femoral head is attached. In some procedures, a prosthetic cup may be implanted in a prepared acetabular cavity to provide a cavity in which the femoral head or prosthetic femoral head may articulate when the joint is reduced. Surgical procedures in which both the acetabulum and at least a part of the femoral head are replaced with prosthetic components are generally referred to as total hip replacement procedures.

During hip surgery procedures, some surgeons may sometimes use one or more trial components, which have the same geometry and size as the intended prosthetic components, so that the surgeon may trial the joint before final implantation of one or both of the prosthetic components. For example, the surgeon may use trial components to check that the size, position or orientation of one or more of the components is suitable. Other surgeons may opt not to use trial components or may use them occasionally based on their professional judgement.

One of the considerations in hip surgery is the angular orientation of the acetabular cavity. When the acetabulum is replaced with an acetabular cup, then it is often an aim of the surgeon to place the acetabular cup so that it is pointing generally in a preferred direction or range of directions. The orientation of an acetabular cup is often defined in terms of an angle of abduction (or inclination) and an angle of anteversion.

A variety of approaches have been used to try and assess the angular orientation of an acetabular cup, either a trail or a prosthesis, after placement in the acetabular cavity.

Anatomical approaches may be used in which the surgeon uses either their experience and/or a piece of instrumentation, in order to gauge, by inspection or instrumentation, the angular orientation of the acetabular cup relative to one or more anatomical features of the patient's pelvis. However, there is often limited access to the surgical site, particularly for minimally invasive approaches, and therefore this is often not easy nor accurate.

Other approaches may use markings or other features on the trial or prosthetic components in order to gauge the angular orientation of the acetabular cup relative to the patient's pelvis.

For example "The Ranawat Sign A Specific Maneuver to Assess Component Positioning in Total Hip Arthroplasty", Lucas, David H., and Scott, Richard D., Journal of Orthopaedic Techniques, Vol. 2, No. 2, June 1994, describes a method of intraoperative assessment of component orientation for total hip arthroplasty. With the patient in the true lateral decubitus position, the femur is internally rotated without hip flexion until a flat underside of the prosthetic head (generally perpendicular to the femoral neck) is coplanar with a rim of the acetabular cup. The amount of internal rotation necessary to achieve this position is known as the Ranawat sign and relates to the combined anteversion of the acetabular and femoral components of the joint. For example a Ranawat sign of 45° may correspond to a cup anteversion of 30° and a femoral anteversion of 15°. However, any knee laxity or deformity can influence the interpretation of this value. Also, there may be difficulty in assessing the actual magnitude of the angle of internal rotation. Further, different surgeons may have different approaches to manipulating the patient's leg and also any one surgeon's approach may not easily be reproducible from patient-to-patient either by that same surgeon or by other surgeons.

WO 2009/108683 describes another approach in which markings are applied to a femoral head and in which the surgeon again applies an amount of internal rotation to the patient's leg, during trial reduction, so that the angle between the rim of the acetabular cup and various markings on the femoral head indicates the angular position of the acetabular cup relative to the patient's pelvis. A neutral leg position is used in which the patient's leg is in full, relaxed extension at zero degrees abduction, zero degrees anteversion and approximately 15° internal rotation, or otherwise internally rotated by an amount equal to the amount of version of the natural or artificial femoral neck. Hence, this approach also requires the surgeon to apply a specific amount of internal rotation to the patient's leg. Again, it may be difficult to apply the correct amount of internal rotation, there may be inaccuracies introduced by deformities of the patient's leg and the surgical technique may be difficult to reproduce and/or reliably learn. This is particularly the case for a relatively small angle, 15°, as even a relatively small error in the amount of internal rotation, for example 5°, is a large proportion (33%) of the target internal rotation.

Other approaches and associated instrumentation are described in US 2005/0107799. An accessory for implanting a hip cup, includes a manipulable cup, a manipulation head having a hemispherical portion and a circular rim around it for aligning the manipulable cup in the acetabulum. A device for immobilizing the aligned position of the manipulable cup is provided and allows a guide to be set for alignment of a bone bur and a drive-in instrument for reaming placing the acetabular cavity and placing the cup. In another approach, a manipulable cup is located in the acetabulum and its orientation can be adjusted by a handle until a lip of the manipulable cup is parallel with an equatorial line on a femoral head or a plane on the reverse of a femoral head Hence, apparatus and/or methods making accurate intraoperative assessment of acetabular cup placement simpler, easier and/or more reliable would be beneficial.

A first aspect of the invention provides an adjustable trial femoral head for assessing the anteversion of an acetabular cup relative to a pelvis of a patient, the adjustable trial femoral head comprising: an at least partially spherical body having a bore configured to receive a free end of a femoral neck; and a visual alignment guide mounted on the at least partially spherical body and wherein the orientation of the visual alignment guide relative to the spherical body is adjustable.

The adjustable trial femoral head may further comprise a lock. The lock may be operable to fix the orientation of the visual alignment guide relative to the at least partially spherical body.

The lock may include a grub screw operable to engage a part of the at least partially spherical body to fix the orientation of the visual alignment guide.

The at least partially spherical body may include at least a first indicium. The at least a first indicium may be arranged to indicate a pre-selected anteversion angle of the acetabular cup relative to the pelvis.

The at least partially spherical body may include a plurality of indicia. Each indicium may be arranged to indicate a different respective pre-selected anteversion angle of the acetabular cup relative to the pelvis.

The or each indicium may be in the form of a line. The or each line may extend at least partially in a direction perpendicular to an axis of the bore.

The visual alignment guide may include a part made of an x-ray opaque material.

The part may be in the form of a ring or a part of a ring. The part may be made of a metal or may be metallic.

The visual alignment guide may include a proud portion which stands proud of an adjacent surface of the visual alignment guide. The proud portion may be arranged to engage with a rim of an acetabular cup or acetabular cup liner in use.

The visual alignment guide may be a part of a cap which is pivotally mounted on the at least partially spherical body.

The visual alignment guide may be a rim or a part of a rim of the cap.

The orientation of the visual alignment guide relative to the spherical body may indicate the anteversion of an acetabular cup relative to the pelvis of the patient when the trial femoral head is mounted on a femoral neck which is attached to the femur of the patient, the adjustable trial femoral head is received in the acetabular cup to form a trial hip joint and wherein the leg of the patient and the pelvis of the patient are arranged in a pre selected position.

The preselected position may be the Ranawat sign position.

The preselected position may be the anatomical position.

The at least partially spherical body may include at least a first indicium, the at least a first indicium being arranged to indicate a 20° anteversion angle of the acetabular cup relative to the pelvis.

The anatomical position may correspond to substantially 0° extension/flexion of the leg, 0° abduction/adduction of the femur and 0° rotation of the femur.

A second aspect of the invention provides a kit of parts comprising one or more of the adjustable trial femoral head of the first aspect of the invention, a trial neck to which the adjustable trial femoral head can be attached, an acetabular cup defining a cup cavity adapted to receive the adjustable trial femoral head; and a femoral part to which the trial neck can be attached.

The kit of parts may further comprise a liner, and wherein the liner defines a liner cavity adapted to receive the adjustable trial femoral head, and the acetabular cup cavity is adapted to receive the liner.

A third aspect of the invention provides a trial hip assembly. The trial hip assembly may comprise the adjustable trial femoral head of the first aspect of the invention and a femoral neck. The trial hip assembly may comprise an assembly of the kit of parts of the second aspect of the invention.

A fourth aspect of the invention provides a method of assessing the anteversion of an acetabular cup within an acetabulum of a pelvis of a patient, comprising: reducing a trail hip joint comprising an acetabular cup within an acetabulum of a pelvis of a patient and an adjustable trial femoral head attached to the neck of a femoral part located within a femur of a leg of the patient, wherein the adjustable trial femoral head includes a visual alignment guide having an orientation which is adjustable relative to the adjustable trial femoral head; and assessing the anteversion of the acetabular cup based on the orientation of the visual alignment guide relative to the adjustable trial femoral head.

The method may further comprise: moving the leg of the patient into an anatomical position before assessing the anteversion of the acetabular cup.

The anatomical position may correspond substantially to 0° extension/flexion of the leg, 0° abduction/adduction of the femur and 0° rotation of the femur.

The visual alignment guide may include a component which is X-ray opaque, and the method may further comprising; capturing an X-ray image of the trial hip joint; and further assessing the anteversion of the cup from the X-ray image.

The visual alignment guide may be free to vary its orientation relative to the adjustable trial femoral head.

The method may further comprise: adjusting the orientation of the visual alignment guide relative to the adjustable trial femoral head; and/or locking the orientation of the visual alignment guide relative to the adjustable trial femoral head.

The adjustable femoral trial head may include at least one indicium corresponding to a preselected anteversion of the acetabular cup and the orientation of the visual alignment guide may be adjusted to align the visual alignment guide with the indicium.

The adjustable femoral trial head may include a plurality of indicia each corresponding to a respective preselected anteversion of the acetabular cup and the orientation of the visual alignment guide may be adjusted to align the visual alignment guide with a one of the plurality of indicia.

The one of the plurality of indicia may correspond to a preselected position of the trial hip joint, and the method may further comprise placing the trial hip joint in the preselected position before assessing the anteversion of the acetabular cup.

Embodiments of the invention will now be described, by way of example only, and with reference to the accompanying drawings, in which:

FIG. 5 shows a coronal view of a pelvis;

FIG. 6 shows a sagittal view of the pelvis of FIG. 5;

FIG. 7 shows a transverse view of the pelvis of FIGS. 5 and 6;

FIG. 8 shows a partial cross sectional perspective view of the pelvis along line A-A of FIG. 5;

FIG. 9 shows a perspective view of the pelvis;

Figure 16:
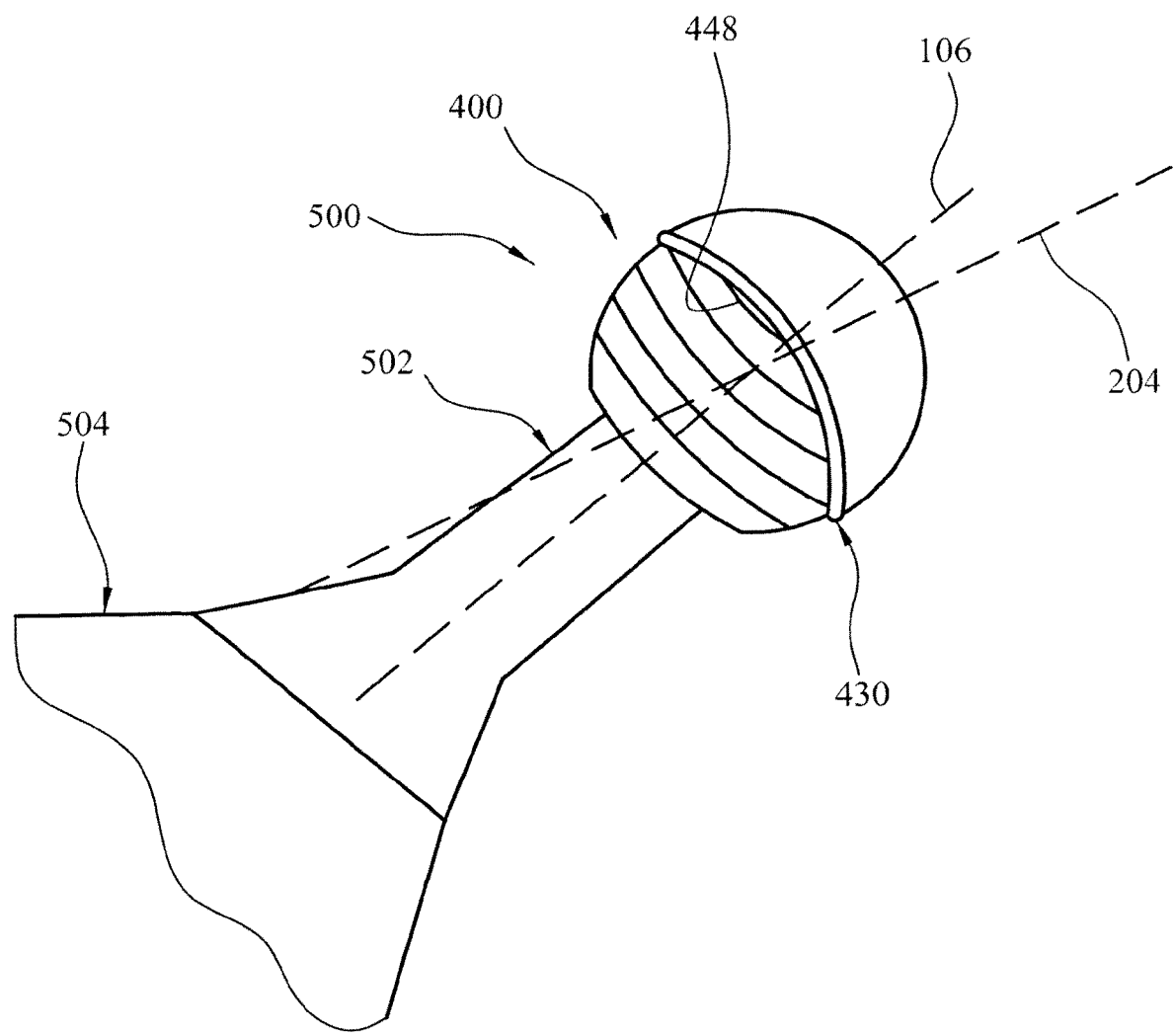
Figure 17:
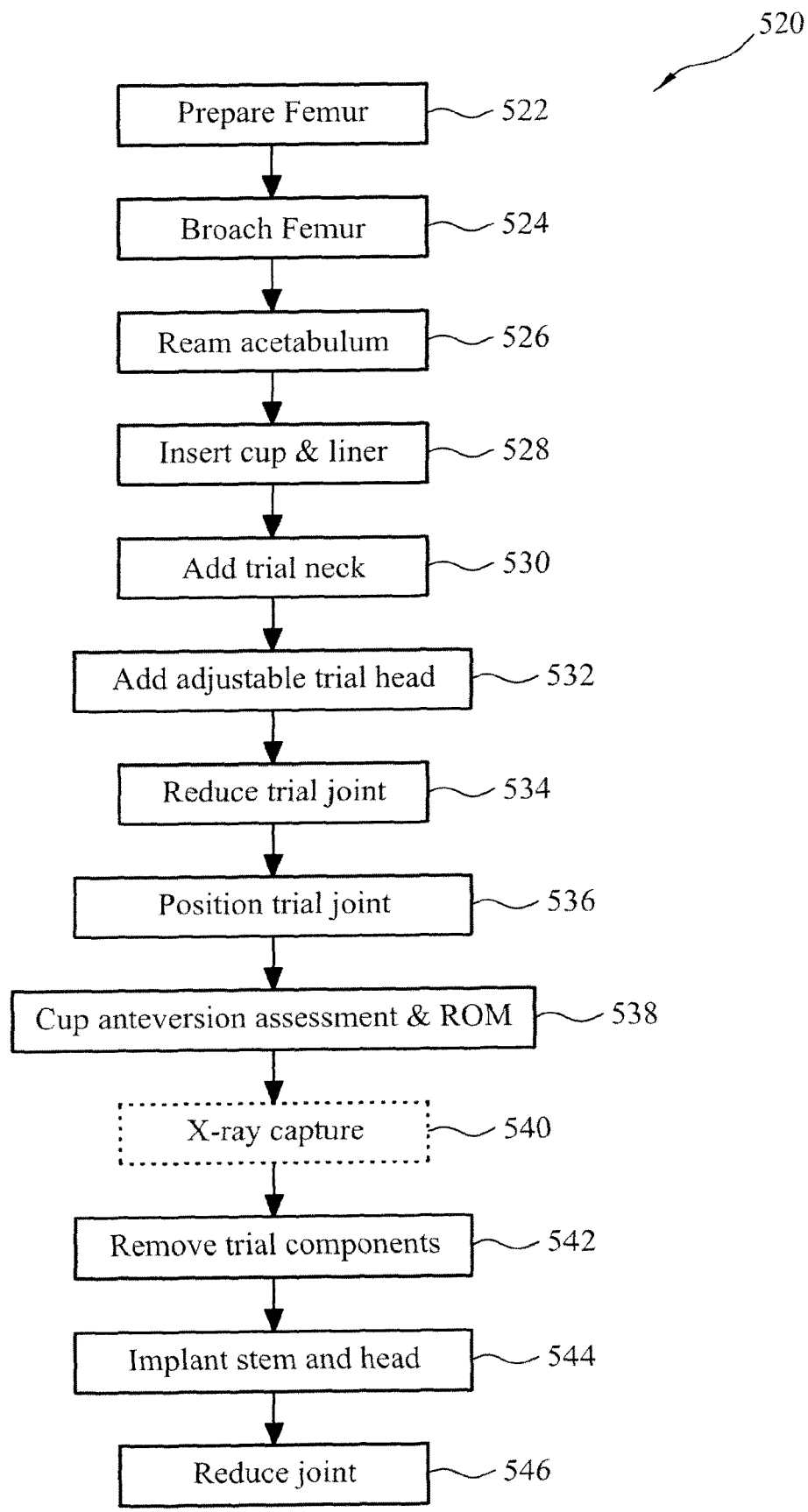

FIG. 16 shows a schematic view in the anterior-posterior of a trial hip joint assembly according to an aspect of the invention and including the adjustable trial femoral head shown in FIGS. 10 to 14; and FIG. 17 shows a flow chart illustrating an embodiment of surgical method according to an aspect of the invention in which the adjustable trial femoral head and trial hip joint assembly may be used to assess a prosthetic cup anteversion.

Similar items in the different Figures share common reference signs unless indicated otherwise.

Before describing the apparatus and/or methods of the invention, the geometry of a hip joint will be discussed generally. In the below, a right hip joint is described, but it will be appreciated that a similar discussion applies to a left hip joint. Also, the following discussion is intended to relate to both the pre-operative natural or native, hip joint, as well as to the artificial, or prosthetic, hip joint. Hence, although the magnitude of the various angles may vary between the native hip joint and the prosthetic hip joint, the definitions of those angles may be generally the same for the native and prosthetic hip and may be determined by the positions and/or orientations of the various parts making up the native hip joint and prosthetic hip joint respectively.

Figure 1:
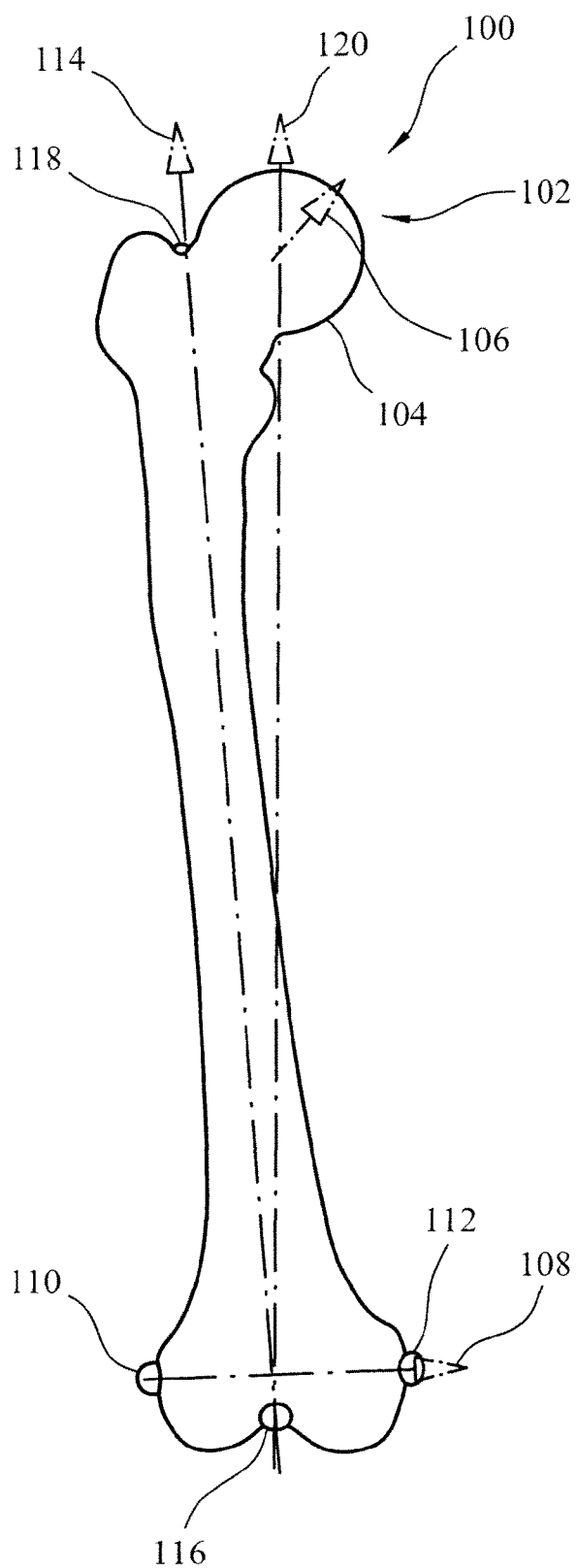
FIG. 1 shows a coronal view of a femur.
Figure 2:
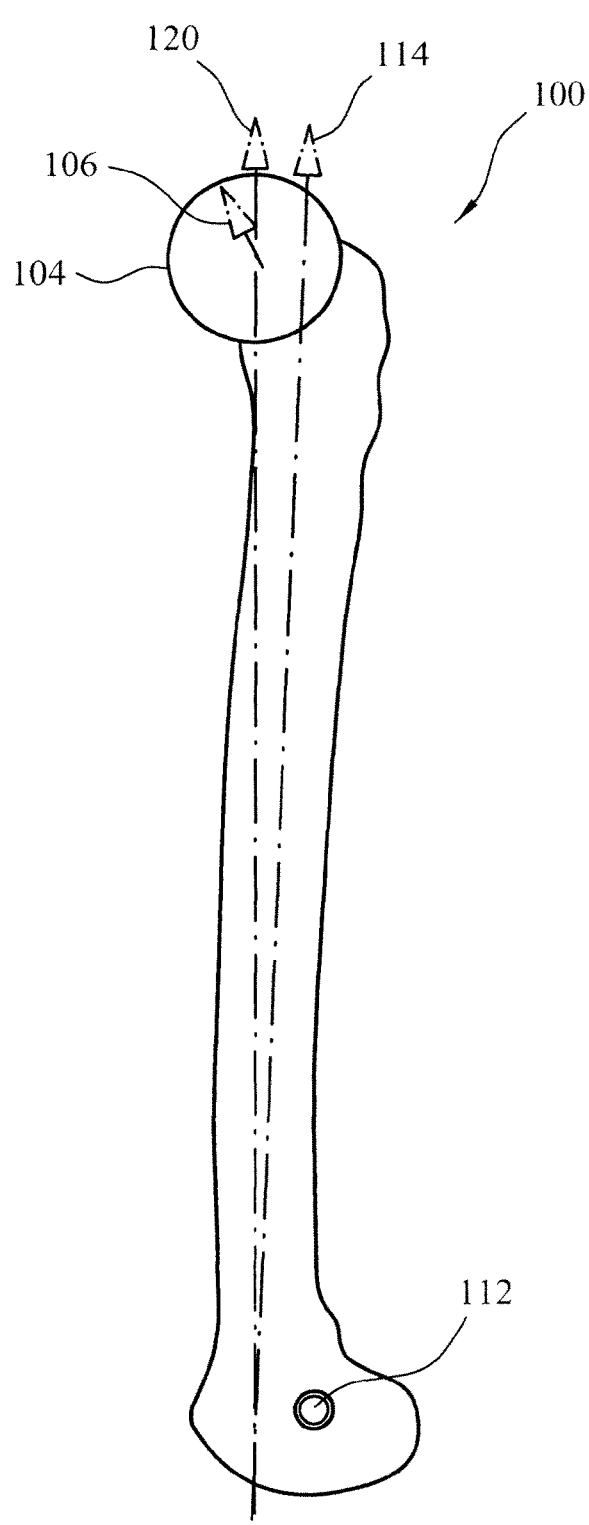
FIG. 2 shows a sagittal view of the femur of FIG. 1.
Figures 3, 4:
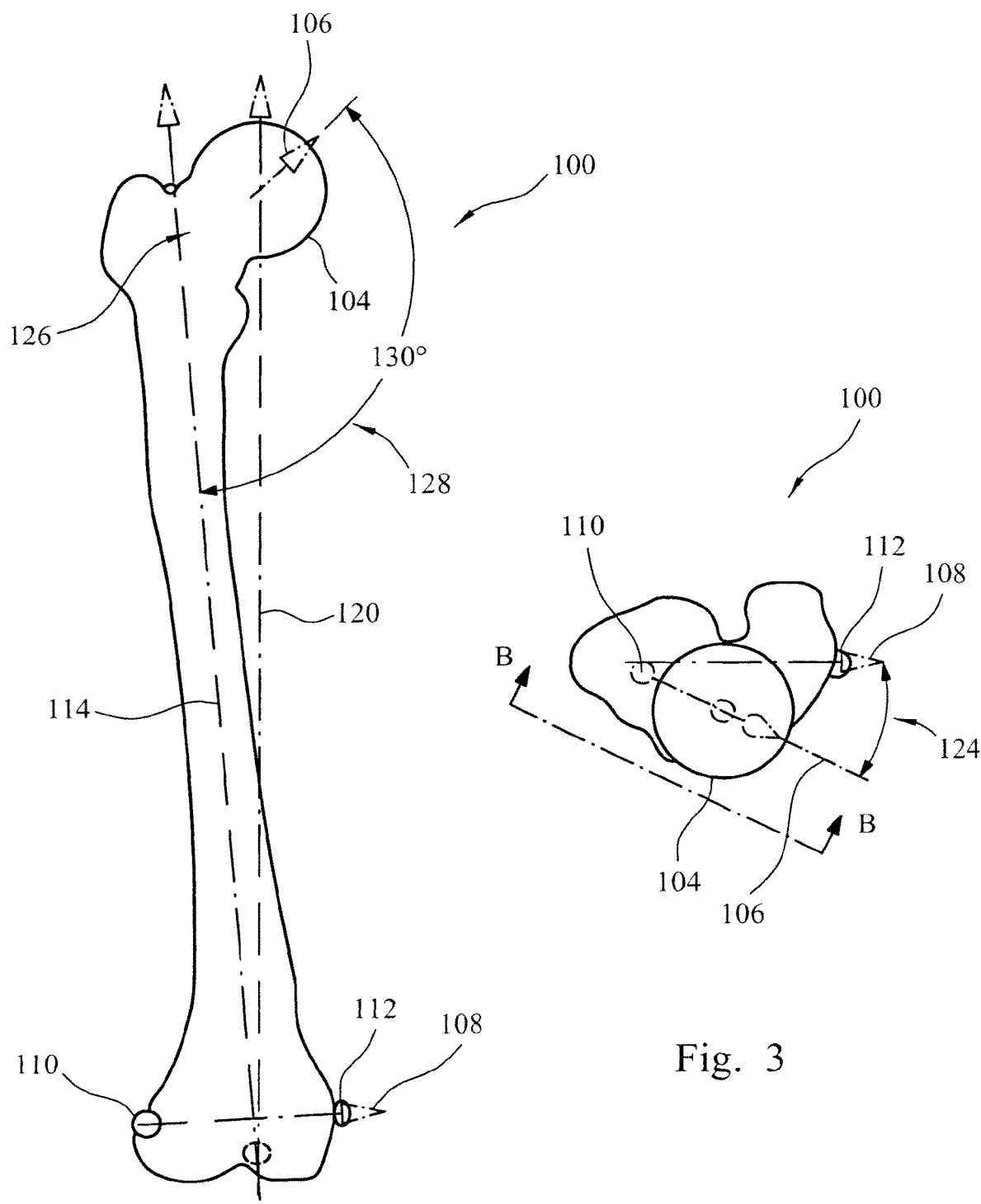
FIG. 3 shows a transverse view of the femur of FIGS. 1 and 2.
FIG. 4 shows a view of the femur in a plane parallel to the anatomic axis and the neck of the femur.

With reference to FIGS. 1 to 4, there are shown various different views of a right femur 100. In particular FIG. 1 shows a coronal view in the anterior to the posterior direction (generally herein the AP direction), FIG. 2 shows a sagittal view in the medial to the lateral direction (generally herein the ML direction), FIG. 3 shows a transverse view in the superior to the inferior direction, and FIG. 4 shows a view of the femur in a plane parallel to the anatomic axis of the femur and the neck of the femur as explained in greater detail below. Pre-operatively, the proximal part of the femur 100 includes the native femoral neck and native femoral head. Intra-operatively and post-operatively the proximal part of the femur may include various trial or prosthetic parts or components providing trial or prosthetic femoral necks and femoral heads. The following will refer generally to femoral necks and femoral heads and is intended to include native, trial or prosthetic ones.

With particular reference to FIGS. 1 and 2, the proximal part 102 of femur 100 includes a femoral head 104 (represented by a sphere) attached to a femoral neck 126, best illustrated in FIG. 4, having a neck axis extending generally in the direction of arrow 106. The femur 100 has an epicondylar axis 108 extending between the lateral femoral epicondyle 110 and the medial femoral epicondyle 112. The femur 100 also has an anatomic axis 114 extending between, for example, the distal femur intercondylar notch 116 and the piriformis fossa, close to the medial face of the greater trochanter. The femur 100 also has a mechanical axis 120 extending between, for example, close to the distal femur intercondylar notch 116 and the centre of the femoral head 104. The anatomical axis 114 and mechanical axis 120 of the femur 100 may be defined by other anatomical points in other embodiments.

With reference to FIG. 3, a femoral neck anteversion angle 124 can be defined as the angle in the transverse plane subtended by the femoral neck axis 106 and the epicondylar axis 108. In practice, the femoral neck anteversion angle for the native neck is typically in the range of about 12° to 15°, but may have other values. Neck anteversion angle 124 is a measure of the anteversion of the femoral neck relative to the local anatomy of the femur 100.

FIG. 4 shows a view of the femur 100 in a plane parallel to line BB of FIG. 3, which is parallel to the femoral neck axis 106, and the anatomical axis 114, and which more clearly shows the femoral neck 126. FIG. 4 also illustrates the neck angle 128 subtended between the femoral neck axis 106 and the anatomical axis 114 of the femur. The native neck angle 128 varies from patient to patient, but is typically about 130°. The neck angle 128 for a trial or prosthetic implant is usually fixed by the implant design, unless the implant is adjustable, and is often intended to approximately reproduce the native geometry and so may also be about 130°. In the following a neck angle 128 of 130° may be used as an example, but it will be appreciated that in other embodiments, other neck angle values may also be used.

Hence during hip surgery in which a prosthetic femoral component is used, one of the variables is the femoral neck anteversion angle 124, which generally measures how far forward the femoral neck 126 is directed compared to the medial-lateral axis of the femur.

With reference to FIGS. 5 to 9, there are shown various different views of a pelvis 200 and right acetabulum. In particular FIG. 5 shows a coronal view in the anterior to the posterior direction (generally herein the AP direction), FIG. 6 shows a sagittal view in the medial to the lateral direction (generally herein the ML direction), FIG. 7 shows a transverse view in the superior to the inferior direction, FIG. 8 shows a partial sectional view along line A-A of FIG. 5, and FIG. 9 shows a perspective view of the pelvis 200 with the anterior pelvic plane (APP) vertical and the transverse axis generally horizontal. Pre-operatively, the pelvis 200 includes an acetabulum which provides a native socket in which the native femoral head is received and articulates. Intra-operatively and/or post-operatively the pelvis may include various trial or prosthetic implants, such as trial or prosthetic acetabular cups (with or without liners depending on the specific implant system being used). The following will refer generally to the acetabulum or acetabular cup and is intended to include the native acetabulum as well as trial or prosthetic components.

As illustrated in FIG. 5, the acetabulum 202 may be represented by a hemisphere or hemispherical cup which generally has a position and an orientation. The orientation or direction of the acetabulum may generally be defined by two angles. A first angle indicates how much the acetabulum is directed forward or backward (generally referred to as anteversion when pointing anteriorly and retroversion when pointed posteriorly) relative to the pelvis. A second angle indicates how much the acetabulum is pointing downward or in an inferior direction (generally referred to as inclination or abduction) relative to the pelvis. The direction of the acetabulum may be defined by an acetabular axis 204, best illustrated in FIG. 9, which generally passes through the centre of the mouth of the acetabulum and perpendicular to the plane of the mouth of the acetabulum.

The pelvis 200 includes a transverse axis 206 passing between the right ASIS 208 and the left ASIS 210. An anterior pelvic plane 212 (generally referred to as APP in the following) is defined by the transverse axis 206 and first and second points on the symphysis pubis 214, 216.

As best illustrated in FIG. 5, an inclination angle for the acetabulum or acetabular cup 202 may be defined by the angle 220 subtended by the transverse axis 206 and a long axis, or inclination axis, 222 of the acetabular cup 202 within, or parallel to, the anterior pelvic plane 212. In FIG. 5, the illustrated inclination angle 220 is approximately 40°. FIG. 8 shows a view of a cross section of the pelvis 200 along line A-A in FIG. 5 and in a direction along the long axis 222 of the acetabular cup 202. Hence, FIG. 8 shows the plane generally perpendicular to the long axis 222 of the pelvic cup 202. From FIG. 8, an anteversion angle 224 may be defined as the angle subtended between the plane 226 of the mouth of the acetabular cup and a plane 228 perpendicular to the anterior acetabular plane 212. Hence, as illustrated in FIG. 8, the acetabulum or acetabular cup 202 has an anteversion angle 224 of approximately 20°.

Hence, as illustrated in the perspective view of the pelvis 200 in FIG. 9, the acetabulum or acetabular cup 202 has an orientation corresponding to an inclination of 40° and an anteversion of 20°. These angles may be referred to as radiographic angles as they are based on the APP view of the pelvis illustrated in FIG. 5 and which is the view of the pelvis typically radiographically imaged or X-rayed and which images are often used by surgeons pre-, intra- and/or post operatively to assess acetabular orientation.

Figure 10:
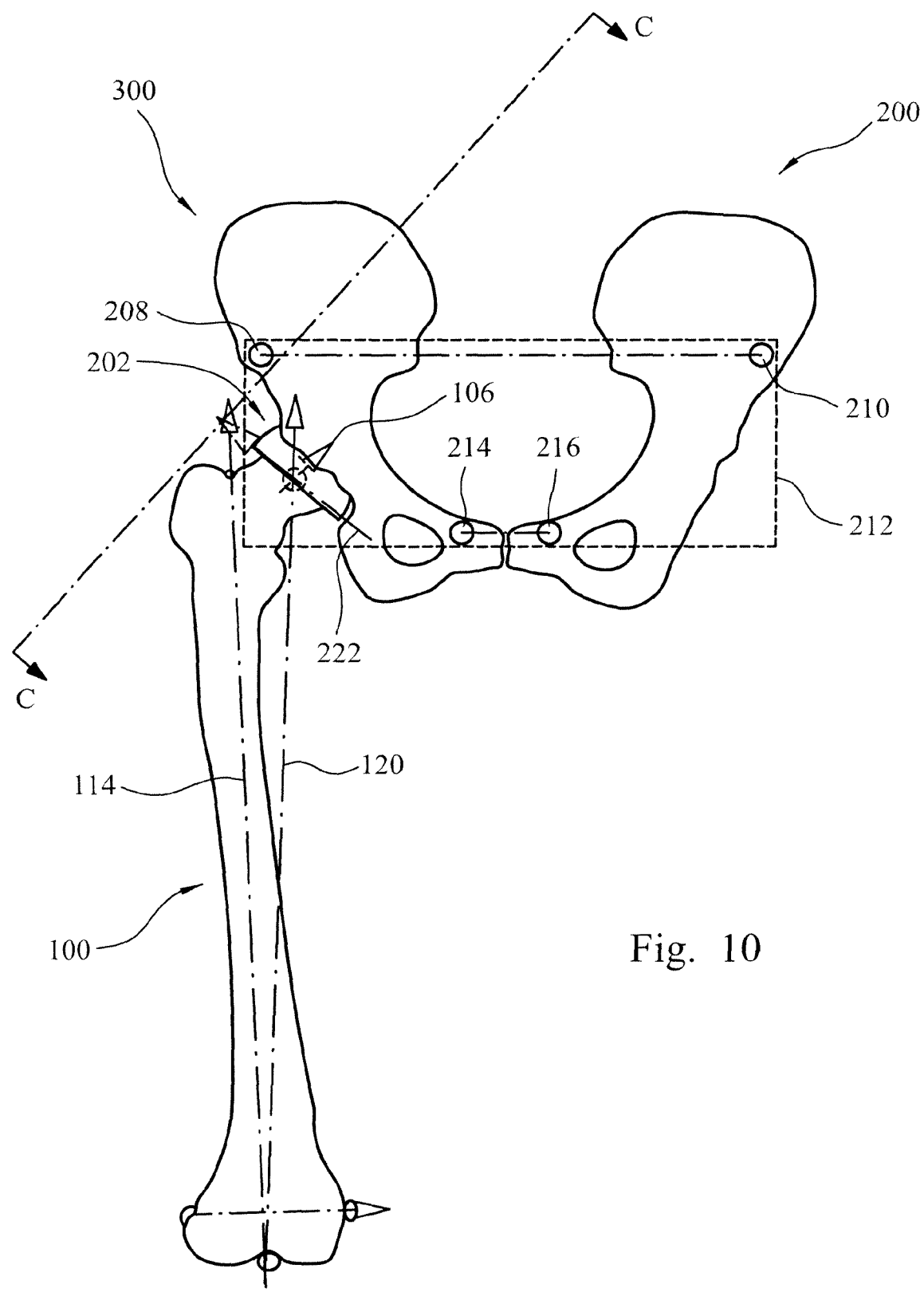
FIG. 10 shows a coronal view of a hip comprising the femur of FIGS. 1 to 4 and the pelvis of FIGS. 5 to 9.
Figure 11:
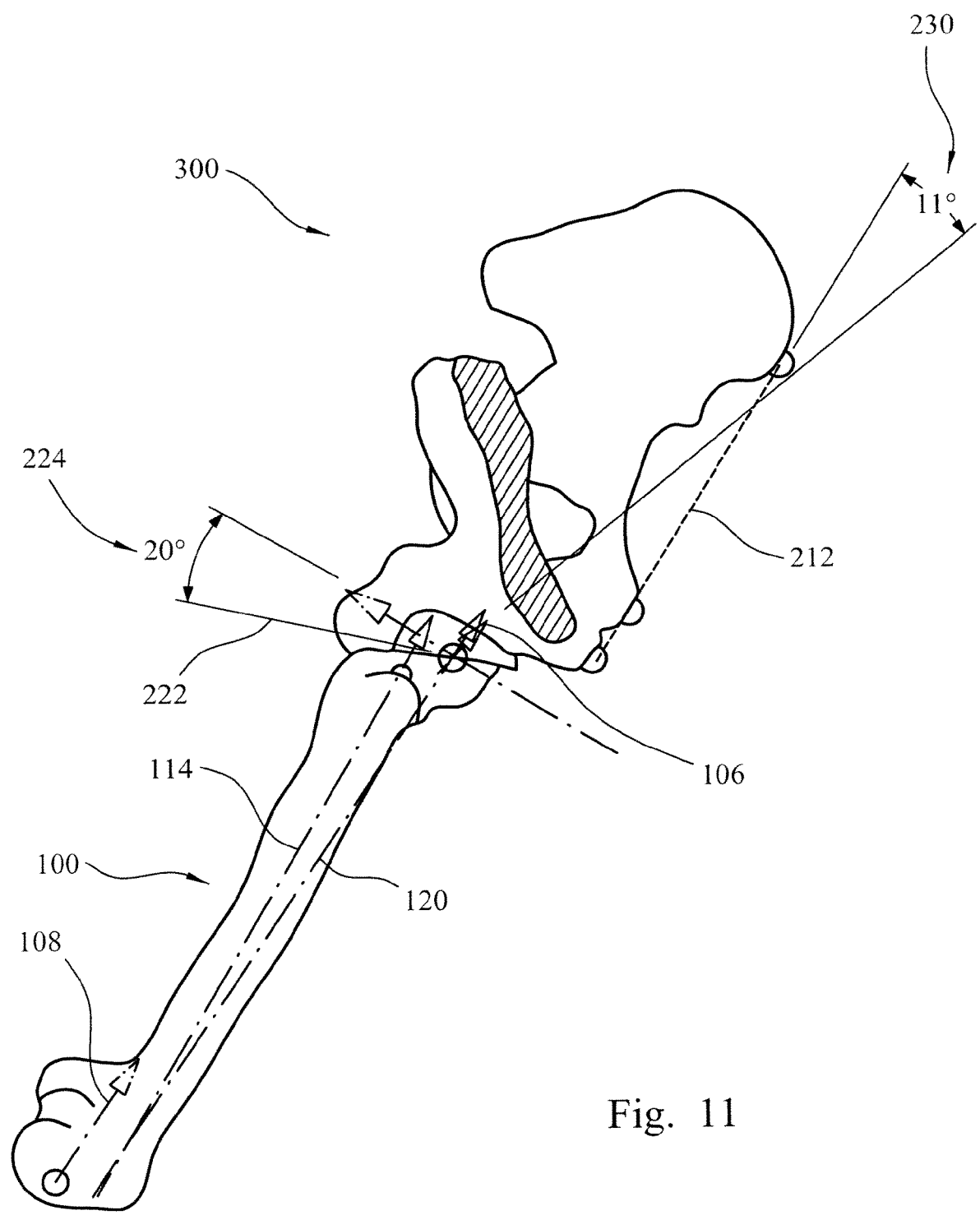
FIG. 11 shows a partial cross sectional perspective view of the pelvis along line C-C of FIG. 10.

With reference to FIGS. 10 to 11, there are shown various different views of a right hip joint 300 formed by femur 100 and pelvis 200. In particular, FIG. 10 shows a coronal view in the anterior to the posterior direction (generally herein the AP direction), similar to FIGS. 1 and 5 combined. In FIG. 10, the femur has been placed in an anatomical position as described in greater detail below. FIG. 11 shows a partial section along line C-C of FIG. 10 and viewed in a direction along the inclination axis 222 of the acetabular cup 202. Hence, the plane of FIG. 11 is generally perpendicular to the direction of the inclination axis 222 of the acetabular cup.

As illustrated in FIG. 11, the acetabular cup 202 has an anteversion angle 224 of 20° in the plane perpendicular to the inclination axis 222 of the acetabulum. FIG. 11 also illustrates the femoral anteversion angle 230 in the plane perpendicular to the inclination axis of the acetabulum and being defined by the angle 230 subtended in that plane by the femoral neck axis 106 and the anterior pelvic plane 212. As illustrated in FIG. 11, the apparent femoral anteversion angle 230 is approximately 11°.

Hence, as can be seen the overall geometry of the hip joint arises from the orientation of the acetabulum relative to the pelvis and also the orientation of the femoral neck relative to the femur. In the illustrated example, the overall or combined anteversion of the hip joint 200 shown in FIGS. 10 and 11 is the combination of the acetabular anteversion, about 20°, and the amount of femoral anteversion projected into the same plane, which in this example is approximately 11°. Hence, the combined anteversion of the hip joint 300 in this plane is about 31°.

However, in practice, when surgeons talk about a combined anteversion of about 35°, this may be arrived at by adding absolute values of angles in different planes, 15° anteversion of the neck relative to the femur in a first plane and 20° anteversion of the acetabulum relative to the pelvis in a second, different plane, to give approximately 35°. In practice, the combined anteversion is assumed to be in the range of approximately 30° to 40°, as being typically greater than 30° and less than 40°, and that any measurement or assessment is likely to be accurate to plus or minus a few degrees anyway and so measurement of the angles in different, non-parallel planes is not crucial.

Herein, combined anteversion may refer, depending on the context, to the general idea that the anteversion of a hip joint is the combined effect of the degree of anteversion of the femoral neck relative to the femur and also the degree of anteversion of the acetabulum relative to the pelvis. More specifically, for non-extreme cases, combined anteversion may also refer to a general rule of thumb that the sum of the acetabular anteversion and the femoral anteversion, measured in the same plane, should have a certain value, for example approximately 35°. Hence, if a low value of one occurs, then the other can be increased (or vice versa) in order to bring the combined anteversion closer to this target value.

While there can be a reasonable degree of adjustment of the orientation of the acetabular cup in the reamed acetabulum, there is less freedom to vary the orientation of the femoral stem. This is because once the proximal part of the femur has been resected and the intramedullary canal reamed or otherwise prepared, there is little remaining bone stock. Hence, there is little freedom in how the surgeon can orient the stem in order to adjust the version of the neck. Hence, in some surgical approaches, a "stem first" approach may be used in which the stem component's position and orientation are determined first. Then, based on the position and orientation of the stem component, the position and/or orientation of the cup may be adjusted particularly as there is greater flexibility in the orientation of the cup within the acetabulum.

Figure 12:
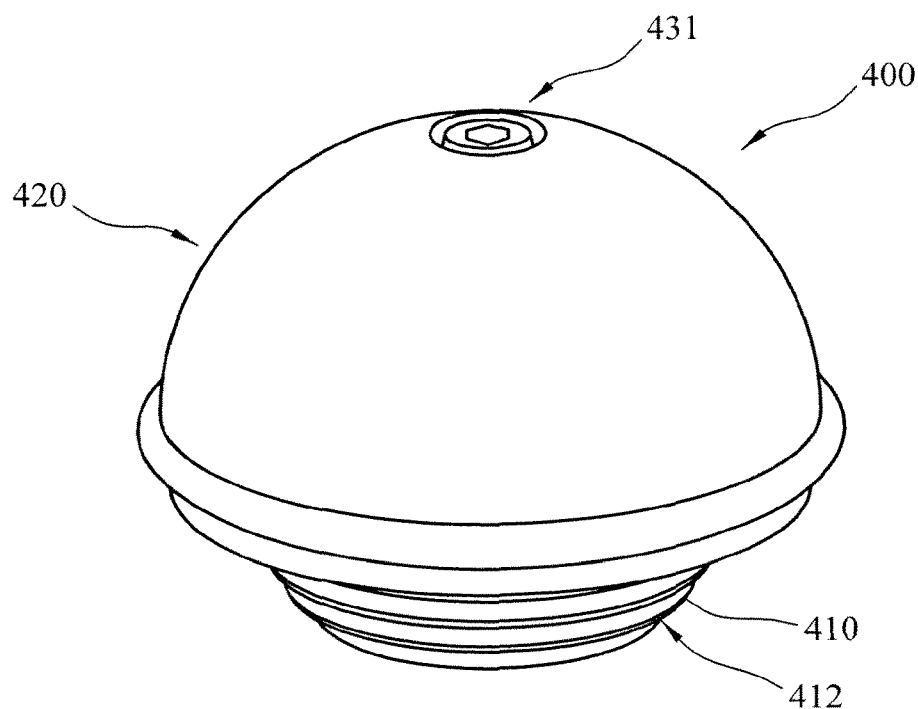
FIG. 12 shows a perspective view of an embodiment of an adjustable trial femoral head according to an aspect of the invention.
Figure 13:
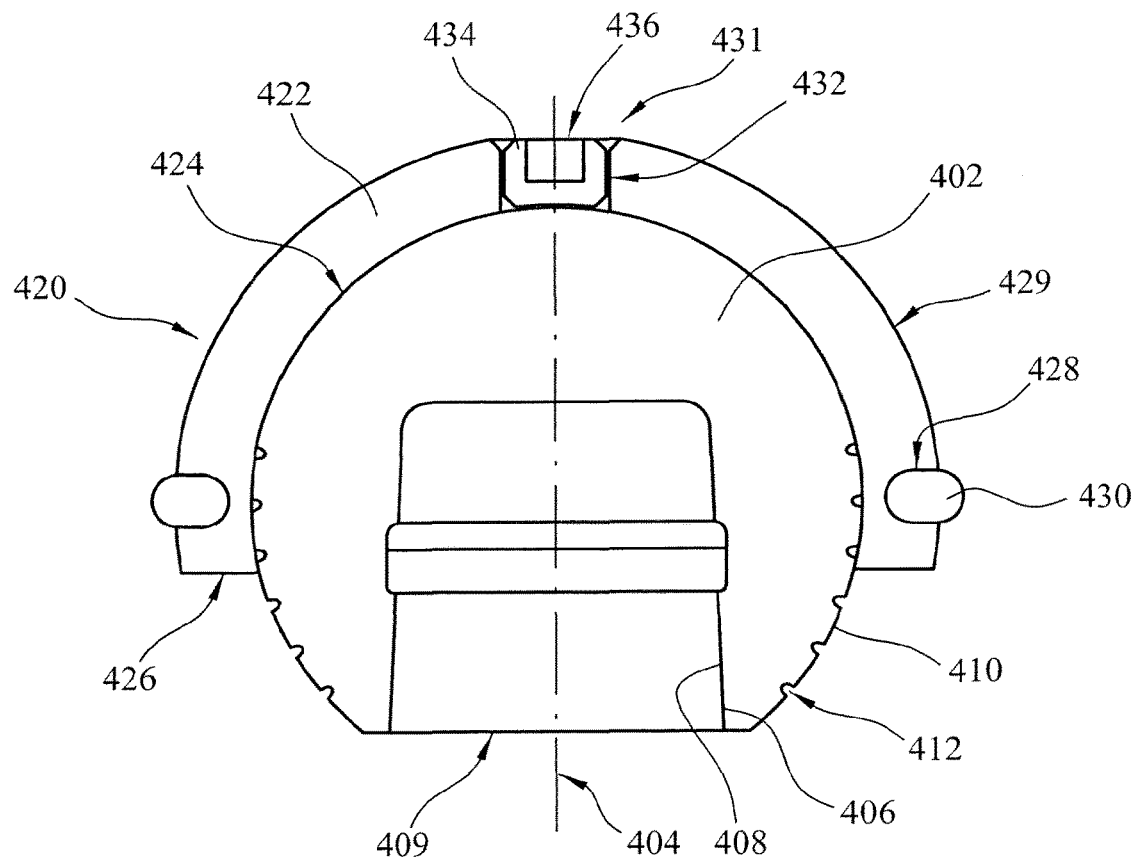
FIG. 13 shows a cross sectional view of the adjustable trial femoral head shown in FIG. 12.

FIG. 12 shows a perspective view of an embodiment of an adjustable trial femoral head 400 according to the invention and FIG. 13 shows a cross sectional view. As best illustrated in FIG. 13, the adjustable trial femoral head includes a body 402 having the shape of a truncated sphere. Generally spherical body 402 has a trial head axis 404 which passes through a pole of the spherical body and through the centre of the spherical body and perpendicularly to the truncated lower surface 406 of the spherical body. An inner wall 408 of the spherical body 402 defines a tapered bore 409 extending along the trail head axis 404. The tapered bore 409 is configured to receive a taper of a femoral neck as will be described in greater detail below. The tapered bore 409 provides a part of a releasable attachment mechanism by which the adjustable trial femoral head 400 may be releasably attached to a femoral neck in use. An outer surface 410 of the spherical body bears a plurality of indicia in the form of a plurality of parallel grooves extending around the outer surface of the spherical body and in a direction generally perpendicular to the trail head axis 404. Each of the plurality of grooves, e.g. groove 412, corresponds to a line of constant latitude of the surface of the spherical body 402.

The adjustable trial femoral head 400 also includes an adjustable visual alignment guide 420. The adjustable alignment guide 420 is in the form of a cap. The adjustable alignment guide 420 is retained on the spherical body 402 and can pivot or tilt about the spherical body 402, with two angular degrees of freedom, and can also rotate relative to the spherical body, for example about trial head axis 404 in the configuration illustrated in FIG. 13. The adjustable alignment guide 420 is in the form of a slightly greater than hemispherical shell and has a cap wall 422. An inner surface 424 of the cap wall 422 defines a truncated spherical cavity within which the spherical body 402 is snugly and pivotably received. A rim 426 of the cap 420 provides an index for the visual alignment guide 420 as will be described in greater detail below. A channel 428 in the outer surface 429 of the cap extends around the equator of the cap. A proud formation extends from the equatorial channel 228 and may be in the form of a circular ring or band 430. The circular ring or band may be in the form of a C-clip or similar. The circular ring 430 may be made from an at least partially X-ray opaque material, for example a metal such as stainless steel. In other embodiments, the circular ring may be made from other materials, such as a plastic, for example polyacetal or polyamide.

The adjustable alignment guide 420 also includes a lock 431 which is actuable to fix the orientation of the adjustable alignment guide 420 relative to the spherical body 402. In the illustrated embodiment, the lock is provided by a threaded bore 432 located in the cap wall 422 at a pole of the cap and which receives a threaded grub screw 434 having a hexagonal cavity 436 for receiving a hexagonal headed tool, such as an Alan key or hex headed driver or similar. Hence, by rotating grub screw 434 its lower end may be engaged with and abut a part of the outer surface 410 of the spherical body to prevent the cap from pivoting relative to the spherical body 402 and hence fix the orientation of the visual alignment guide 420 relative to the spherical body 402.

The adjustable trial femoral head allows assessment of the anteversion of the acetabular cup relative to the pelvis, by extrapolating that from a measurement relative to the femur.

Figure 14:
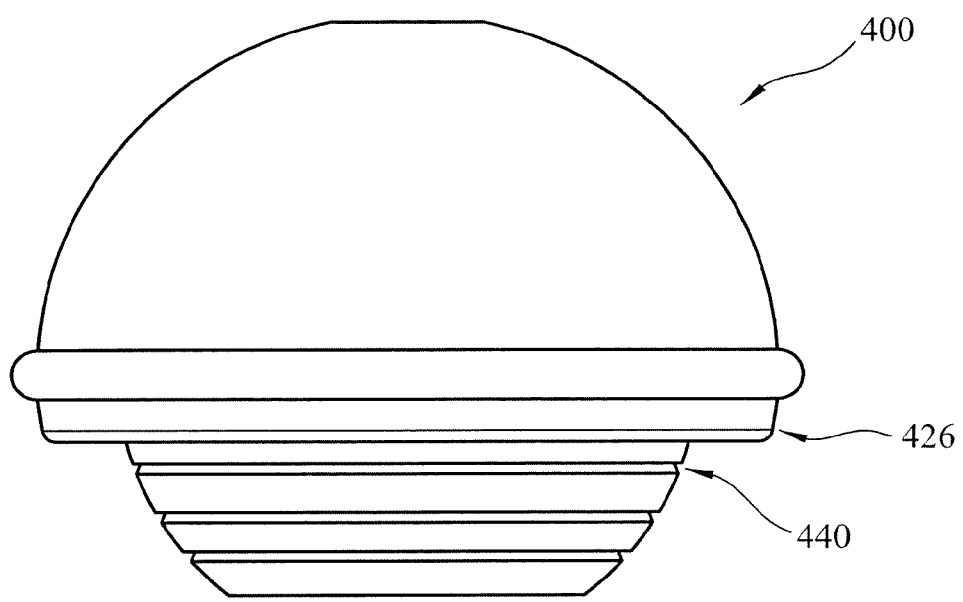
FIG. 14 shows a side view of the adjustable trial femoral head of FIG. 12 with a visual alignment guide at a first orientation.
Figure 15:
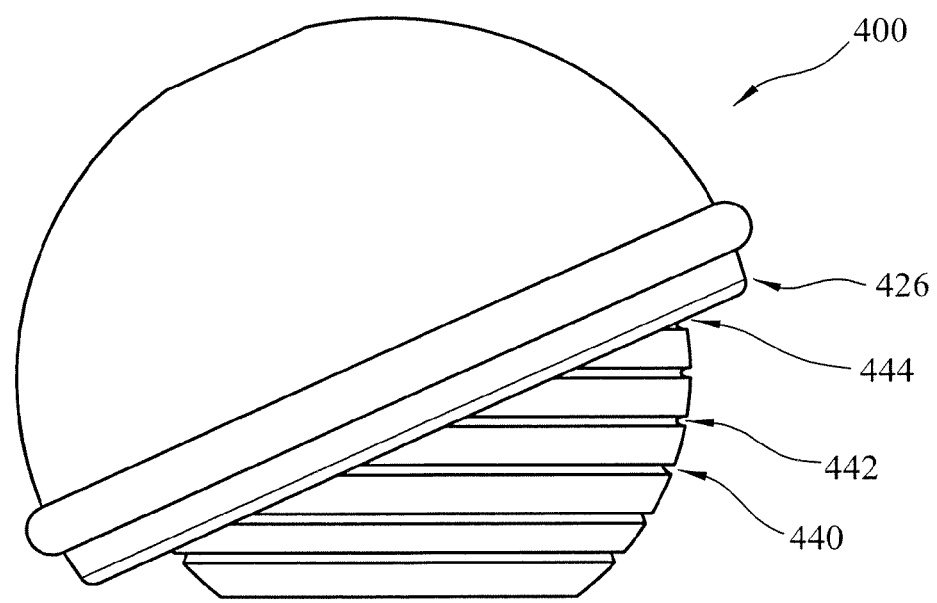
FIG. 15 shows a side view of the adjustable trial femoral head of FIG. 12 with the visual alignment guide at a second orientation.

FIG. 14 shows a side view of the adjustable trial femoral head 400 in a first configuration and FIG. 15 shows a further side view of the adjustable trial femoral head 400 in a second configuration. The plurality of grooves in the outer surface of the spherical body provide a visible scale which can be used to assess the degree of anteversion of an acetabular cup with which the adjustable trial femoral head is used. Predominantly the anteversion of the cup is assessed, but the inclination of the cup should also be at or close to the appropriate target inclination angle to accurately measure anteversion and hence the trial femoral head can also provide an indication of the correctness of the inclination as a secondary effect.

Seven grooves are provided in the example shown in FIGS. 12 to 15 and the angular difference between adjacent grooves may be 5°. The rim 426 of the cap provides a movable index against which the angular scale provided by the grooves can be read.

Hence, the adjustable trial femoral head in the first configuration illustrated in FIG. 14, with the rim 426 between the third 440 and the fourth 442 grooves, corresponds to an acetabular cup version relative to the pelvis of approximately 15 degrees of retroversion if the femur is in the normal range and so −15° of anteversion when the adjustable trial femoral head is located in the acetabular cup, with the proud formation 430 seated against the rim of the acetabular cup, or any cup liner, and with the trial joint in a pre-selected position. One pre-selected trial joint position may be the anatomical position, described in greater detail below, but other pre-selected positions may also be used.

For example, if the Ranawat sign position were used, then the scale could stay the same but would be read differently. The Ranawat sign position would put the head perpendicular to the cup at 35° of combined anteversion so if used with the Ranawat sign position, then the scale would indicate the error relative to Ranawat sign. Hence, if the Ranawat sign position corresponded to 35°, then the sale marking would indicate the angular variance from 35°.

The adjustable trial femoral head in the second configuration illustrated in FIG. 15, with the rim 426 adjacent the sixth groove 444, corresponds to a different acetabular cup anteversion relative to the pelvis of approximately 15° to 20° when the adjustable trial femoral head is located in the acetabular cup, with the proud formation 230 seated against the rim of the acetabular cup, or any cup liner, and with the trial joint in the same anatomical position.

The adjustable trial femoral head 400 may generally be used in two ways. In a first way, the orientation of the cap 420 relative to the spherical body 402 may be adjusted, to position the rim 426, relative to the angular scale to set a desired or target angle of cup anteversion and then the orientation of the cap 420 may be locked by using a tool to adjust grub screw 434. Hence, the surgeon can select a desired or target anteversion angle for the acetabular cup on a patient-by-patient basis by adjusting and locking the orientation of the cap 420 to provide a visual indication of how well the cup is aligned with the desired or target cup anteversion angle, e.g. 20° anteversion relative to the pelvis, when the trial hip joint is reduced and arranged in the anatomical position. Hence, the adjustable trial femoral head 400 can be adjusted for different target anteversion angles for the same pre-selected trial joint position.

Additionally, or alternatively, the surgeon can select and fix the orientation of the cap 420 relative to the body 402, depending on the pre-selected position of the trial joint to be used for the assessment of acetabular cup orientation. The surgeon may decide to use a different trial joint positon, for example because they are using a different surgical approach (with the patient in a different position), or simply a different trial joint position which they are familiar with, or which is convenient for the particular patient. Hence the surgeon may adjust and lock the orientation of the cap 402 to provide a visual indication of when the cup is aligned with the desired or target anteversion angle for the trial hip joint arranged to correspond to the Ranawat sign position, and which corresponds to the configuration shown in FIG. 14. Hence, the adjustable trial femoral head 400 can be adjusted for different pre-selected trial joint positions.

In a second way of using the adjustable trial femoral head 400, the orientation of the cap 420 relative to the spherical body 402 is not locked prior to reduction of the trial joint and positioning of the trial joint in the preselected position. Hence, when the trial joint is reduced, the proud feature 430 will engage the rim of the acetabular cup, or any acetabular cup liner and then the spherical body 402 will pivot within the cap 420 as the patient's leg and/or pelvis are manipulated to position the trial joint in the pre-selected position or configuration. The surgeon may then visually inspect the adjustable trial femoral head to read the anteversion angle of the cup from the position of the index provided by the cap rim 426 on the angular scale provided by the plurality of grooves.

The plurality of indicia providing the angular scale may have a number of variations. For example instead of grooves, lines on the surface may be used additionally or alternatively.

Additionally, or alternatively, colour coding may be used to indicate different specific angular values, or ranges of angular values or acceptable angular values. For example, lines or grooves corresponding to unsafe acetabular cup anteversion angles may be coloured red, while lines or grooves corresponding to border line acetabular cup anteversion angles may be coloured orange, while lines or grooves corresponding to acceptable acetabular cup anteversion angles may be coloured green. Additionally or alternatively, numerical values for the acetabular cup anteversion angles may be included either as absolute values, e.g. 10°, 15°, 20°, 25°, 30°, or as relative values from a preselected target value, e.g. −10°, −5°, 0°, +5°, +10°.

The parts of the adjustable trial femoral head may be made from any suitable biocompatible material, including various metals and plastics. For example suitable polymer materials include polyphenylsulphone, polyacetal, polyamide, polypropylene, polyarylamide, polyetherimide, acrylonitrile-butadiene-styrene, polymethylmethacrylate, polycarbonate, and all polymers could be unfilled or filled with glass or carbon fibres or beads. However, in some embodiments, the ring 430 may be made from a suitable at least partially X-ray opaque material, such as polyphenylsulphone with a barium sulphate embedded in the polymer matrix or any metal powder, the ring 430 may be a fully metallic component, such as stainless steel. The cap 420 has a diameter corresponding to the internal diameter of an acetabular cup, or acetabular cup liner, with which it will be used. For example, typical acetabular cup diameters range from 38 mm to 80 mm, with the typical range being 44 mm to 66 mm. The liners have a slightly smaller diameter so as to fit inside flushly.

FIG. 16 shows a schematic perspective view in the anterior-posterior direction of a trial joint assembly 500 also according to the invention, and including the adjustable trial femoral head 400 of the invention, in use during a surgical method which is illustrated by the flow chart shown in FIG. 17. The trial joint assembly 500 includes the adjustable trial femoral head 400, which is mounted on the taper of a femoral neck 502. In some embodiments, the femoral neck 502 may be a trial femoral neck which is mounted on a femoral part or component 504 which may be a broach or rasp (only a part of which is shown in FIG. 16). In other embodiments, the femoral component 504 may be a trial femoral stem, or a prosthetic femoral stem. The femoral component 504 is oriented in the femur with an anteversion of approximately 15° relative to the femur. The prosthetic acetabular cup (not shown), and which may include a liner, has an acetabular orientation relative to the pelvis as defined by the acetabular axis 204 described above. The trial neck 502 has an orientation defined by the neck axis 106 which extends along the trial neck 502 and corresponds to the trial head axis 404 illustrated in FIG. 13.

FIG. 16 shows the trial joint, formed by the trial femoral components and the acetabular cup, in a pre-selected position, such as the anatomical position described below. The proud feature 430 rests against and around the rim of the acetabular cup, or any liner, and the anteversion of the acetabular cup is visually indicated by the location of the cap rim 426 relative to the angular scale which, in the illustrated example, is the fifth line or groove 448 and which may corresponds to a cup anteversion angle of, e.g., 20° relative to the pelvis.

With reference to FIG. 17, there is shown a flow chart illustrating a hip replacement surgical procedure 520 in which the adjustable trial femoral head, 400, and trial assembly 500, may be used. Many of the steps are common for the locked and the non-locked uses the adjustable trial head. A locked method will be described first. The order of some of the steps is not relevant but the order of some of the steps may be relevant as will become apparent from the following description. Also, some of the described steps may be optional, and may be omitted, depending on the workflow that a surgeon may prefer.

At 522, the femur is prepared in a generally conventional manner which may include resecting the native femoral neck and head and then at 524 a cavity is formed along the intramedullary canal to accept a femoral stem component and which typically includes using one or more broaches and/or rasps. When a final sized broach has been used, then a broach handle is removed and the broach is left in the femur. At 526, the acetabulum is prepared in a generally conventional manner which may include removing soft tissue and forming a hemispherical cavity within the native acetabulum using an acetabular reamer. At 528 a prosthetic acetabular cup is inserted in the acetabular cavity by the surgeon using a cup inserter and with a certain orientation (version and abduction). Any cup liner may also be inserted in the implanted acetabular cup at 528.

At 530, a trial neck 502 is attached to the broach 504. The adjustable trial femoral head 500 is adjusted so that the rim 426 is positioned adjacent the line or groove of the scale corresponding to a target or desired anteversion of the acetabular cup, e.g. the fifth groove or line 448 corresponding to 20°, and then the grub screw is fastened to lock the cap orientation relative to the spherical body 402. The adjustable trial femoral head is then releasably attached to the neck at 532, to form a trial femoral head assembly, by inserting a taper at the free end of trial neck 502 into the tapered bore 408 of the spherical body 402. At 534, the trial joint is reduced by introducing the adjustable trial femoral head 400 into the implanted acetabular cup, or liner. Then at 536, the patient's pelvis and/or leg are manipulated to place the trial joint in the preselected position or configuration.

In particular, the patient's leg is placed with the femur in an anatomical position with respect to the pelvis. Specifically, the femur is placed in 0° of flexion/extension, 0° of adduction/abduction and 0° of internal/external rotation.

Assuming that the pelvis on the operating table has taken up an approximately neutral amount of pelvic tilt then this can be achieved by comparing the following three factors. The long axis of the leg relative to the longitudinal axis of the patient can be adjusted by pulling lightly on the lower limb to pull the leg into full extension. If an anterior approach is being used, with the patient supine, then the leg will naturally rest in full extension. Zero abduction/adduction of the legs can be achieved by placing both lower legs (tibia from knee to ankle) parallel and almost touching. An internal/external rotation angle of 0° can be checked using the epicondyle axis of the knee relative to the transverse axis of the pelvis. If the pelvis is level (supine) or vertical (in a lateral decubitus approach) on the table, then the epicondyle axis can be compared to the table. If a posterior approach is being used, with the patient lateral, then the tibia can be flexed 90° to provide a more discernible indication on the femoral articular axis which will indicate any internal/external rotation of the femur. Hence, depending on the orientation of the patient on the table, the patient's legs are placed in appropriate positions to provide 0° of flexion/extension, 0° of abduction/adduction and 0° of internal/external rotation of the femur with respect to the pelvis. With the patient's legs in this anatomical position, an assessment of the trial cup position can be carried out at step 538.

If the cup has been placed with an orientation having an anteversion relative to the pelvis corresponding to the value to which the adjustable trial femoral head was locked, e.g. 20°, then as illustrated in FIG. 9, the rim 426 of the cap 420 will be generally parallel to the rim of the cup, or liner, and the proud feature 430 will be seated against the rim of the cup, or liner, around its entire rim. Alternatively, if the cup has been placed with an orientation having an anteversion different to the value to which the adjustable trial femoral head was locked, then the rim 426 of the cap 420 will be not be parallel to the rim of the cup, or liner, and the proud feature 230 will be engage just a part of the rim of the cup. Hence, the rim 426 of the cap provides a visual indication of the anteversion angle of the acetabular cup, as the angle subtended between the rim 426 of the cap and the rim of the cup, or liner, indicates generally how far away angularly the cup has been placed compared to the target value. The proud feature 430 may also provide some tactile, or haptic, feedback to the surgeon as they will be able to feel a 'click' as the proud feature 430 rides over the rim of the cup, or liner, as the angle of the patient's leg is changed and the trial head articulates within the cup. Hence, at 538, the surgeon may assess the cup anteversion by visually inspecting the trial joint assembly to see how close the cap rim 426 is to parallel to the cup or liner rim.

Optionally, at step 538 a range of motion (ROM) assessment can also be carried out. This is generally known in the art and involves articulating the trial hip joint to detect the likely range of articulation possible before impingement of the hip components.

At 540 an intra-operative X-ray image of the trial joint in the anterior-posterior direction (corresponding to FIG. 5) may be captured with the trial joint in the preselected position. This X-ray image will capture a projection of the circular ring 430 into the X-ray image plane which is perpendicular to the anterior-posterior axis. The projection of the ring will be an ellipse whose dimensions correspond to the angular orientation of the cup, when the ring 430 abuts the rim of the cup about the whole of the rim of the cup. Hence, the angular orientation of the cup can also be assessed from an X-ray image of the trial joint and ring 430.

It is not necessary that the surgeon carryout any repositioning of the cup. The trial assessment at 538 may be carried out simply to assess the anteversion angle achieved so as to provide so immediate intra-operative feedback of the cup orientation to the surgeon.

At 542, all the trial femoral components, including the broach, are removed from the femur. Then at 544, the actual prosthetic femoral stem is implanted in the femoral cavity and the prosthetic femoral head is attached. Then at 546, the joint can be reduced and any range of motion trial carried out if desired. The surgical procedure then substantially ends.

The overall method 520 is generally similar when the adjustable femoral trial head is not locked prior to reduction of the trial joint at 534. However, in this case, the spherical body 402 is free to articulate within cap 420 whose proud feature 430 abuts against the rim of the cup or any cup liner. Hence, when the patient's leg is moved relative to the pelvis to adopt the anatomical position, the spherical body 402 will pivot and the cup anteversion angle can be read from the position of the cap rim 426 on the scale. Hence, the cup anteversion angle can be assessed by visually inspecting the adjustable trial femoral head, which effective measures the anteversion angle of the cup relative to the pelvis.

When the mobile cap 420 follows the cup liner, then the rim of the cap is compared against the lines/grooves. Assuming that the inclination is set and reasonably close to the target value, then the only indication is going to be anteversion, and the extreme exposed line or groove will indicate the amount of anteversion, e.g. line/groove 448 in FIG. 16.

It will be appreciated that other specific forms of the adjustable visual alignment guide 420 can be used. All that is required is that there is some structure which is pivotable about one or two angular degrees of freedom so that a visual indication of the anteversion angle of the cup can be varied. For example, rather than being in the form of a partially spherical cap, the visual alignment guide may have an annular form, for example in the form of an equatorial band, which extends sufficiently far away from the equator of the spherical body 402, that it is retained on and pivotable about the spherical body.

The adjustable trial femoral head may therefore be adjusted to correspond to various different cup anteversion angles and so the same trial head may be used on a wide range of patients. Additionally, or alternatively, the same trial head may be used for different pre-selected trial joint positions and/or hip replacement procedures for which the patient has different positions on the operating table.

Hence, the invention may make intra-operative cup anteversion orientation assessment easier, quicker, simpler, more quantitative and/or more useful to the surgeon.

In this specification, example embodiments have been presented as particular combinations of features. However, a person of ordinary skill in the art would understand that many other embodiments may be practiced which include a different combination of features, including fewer features or a greater number of features. It is intended that the following claims cover all possible embodiments.

Any instructions and/or flowchart steps may be carried out in any order, unless a specific order is explicitly stated or would be understood to be required from the context of the description. Also, those skilled in the art will recognize that while one example method has been discussed, a variety of other differing methods are possible based on other combinations and/or orders of method steps, and are to be understood within a context provided by this detailed description.

While the inventions are amenable to various modifications and alternative forms, specific embodiments are shown by way of example in the drawings and described in detail. It should be understood, however, that other embodiments, beyond the specific embodiments described, are possible as well. All modifications, equivalents, and alternative embodiments falling within the scope of the appended claims are covered as well.

The invention claimed is:

1. An adjustable trial femoral head for assessing an anteversion of an acetabular cup relative to a pelvis of a patient, the adjustable trial femoral head comprising:

an at least partially spherical body having a bore configured to receive a free end of a femoral neck;

a visual alignment guide mounted on the at least partially spherical body and wherein an orientation of the visual alignment guide relative to the at least partially spherical body is adjustable;

wherein the visual alignment guide comprises a grub screw operable to fix the orientation of the visual alignment guide relative to the at least partially spherical body by engaging the at least partially spherical body to fix the visual alignment guide relative to the at least partially spherical body;

wherein the at least partially spherical body includes a plurality of indicia, each indicium being arranged to indicate a different respective pre-selected anteversion angle of the acetabular cup relative to the pelvis, each indicium being in the form of a line extending perpendicularly relative to a central axis of the bore along lines of constant latitude;

wherein the visual alignment guide comprises a cap pivotally mounted on the at least partially spherical body, the cap comprising a ring which stands proud of an adjacent surface of the cap and which is configured to seat against a rim of an acetabular cup or acetabular cup liner; and wherein the orientation of the visual alignment guide relative to the indicia indicates the anteversion of an acetabular cup relative to the pelvis of the patient when the trial femoral head is mounted on a femoral neck attached to the femur of the patient and the adjustable trial femoral head is received in the acetabular cup to form a trial hip joint and the leg of the patient and the pelvis of the patient are arranged in a pre-selected position.

2. The adjustable trial femoral head of claim 1, wherein the ring is made of an x-ray opaque material.

3. The adjustable trail femoral head of claim 1, wherein the ring is made of a metal.

4. The adjustable trial femoral head of claim 1, wherein the pre-selected position is a Ranawat sign position.

5. The adjustable trial femoral head of claim 1, wherein the pre-selected position is an anatomical position.

6. The adjustable trial femoral head of claim 5, wherein at least one indicium of the indicia is arranged to indicate a 20° anteversion angle of the acetabular cup relative to the pelvis.

7. The adjustable trial femoral head of claim 5, wherein the anatomical position corresponds substantially to 0° extension/flexion of the leg, 0° abduction/adduction of the femur and 0° rotation of the femur.

* * * * *